United States Patent [19]

Klima

[11] Patent Number: 4,788,286

[45] Date of Patent: Nov. 29, 1988

[54] PROCESS FOR OBTAINING SOLID CYANURIC CHLORIDE

[75] Inventor: Hubertus Klima, Tacherting, Fed. Rep. of Germany

[73] Assignee: SKW Trostberg Aktiengesellschaft, Trostberg, Fed. Rep. of Germany

[21] Appl. No.: 111,129

[22] Filed: Oct. 21, 1987

Related U.S. Application Data

[63] Continuation of Ser. No. 854,344, Apr. 21, 1986, abandoned.

[30] Foreign Application Priority Data

Apr. 24, 1985 [DE] Fed. Rep. of Germany ....... 3514840

[51] Int. Cl.$^4$ ........................................... C07D 251/28
[52] U.S. Cl. .................................................. 544/191
[58] Field of Search ........................................ 544/191

[56] References Cited

U.S. PATENT DOCUMENTS 4,533,733  8/1985  Vollbrecht ........................ 544/191
4,535,160  8/1985  Elischer et al. ..................... 544/191

FOREIGN PATENT DOCUMENTS 0137505  4/1985  European Pat. Off. ..
0158362  10/1985  European Pat. Off. ..
1544129  7/1970  Fed. Rep. of Germany .

*Primary Examiner*—John M. Ford
*Attorney, Agent, or Firm*—Felfe & Lynch

[57] ABSTRACT

A process for obtaining solid cyanuric chloride from the cyanuric chloride vapor obtained by trimerizing cyanogen chloride whereby the cyanuric chlorid vapor is introduced into the center of many separated cold annularly disposed inert gas streams in the lower part of the condensor and whereby the solid cyanuric chloride that is obtained on the bottom of the condensor is removed, whereas the heated inert gas is removed at the side. The advantages of the process of the present invention are high condensation throughputs, minor problems with sticking as well as good product quality of the obtained cyanuric chloride.

11 Claims, 1 Drawing Sheet

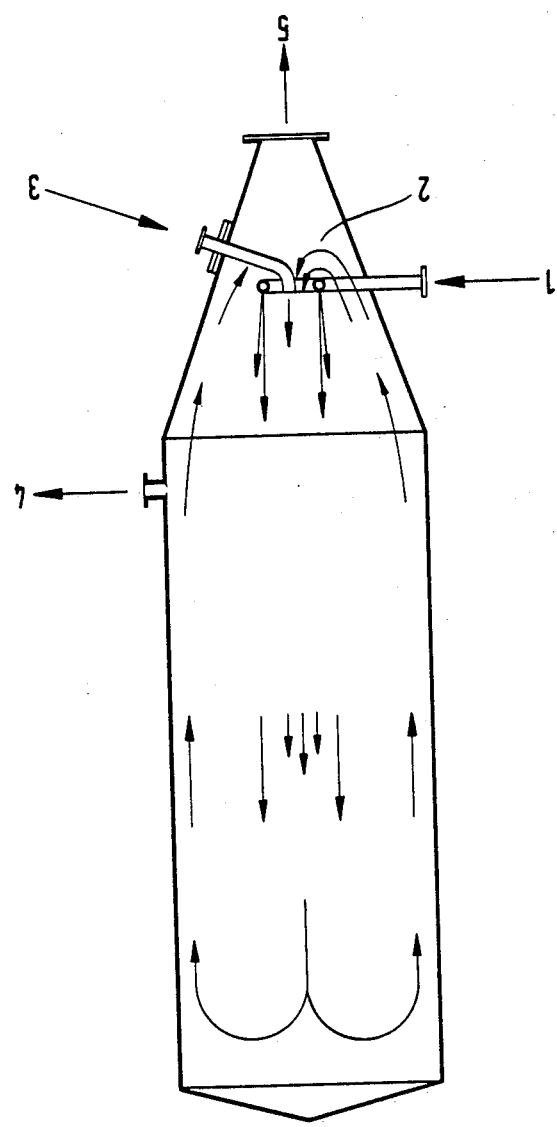

PROCESS FOR OBTAINING SOLID CYANURIC CHLORIDE

This application is a continuation of application Ser. No. 854,344, filed Apr. 21, 1986, now abandoned.

The present invention is concerned with a process for obtaining solid cyanuric chloride from the cyanuric chloride vapor obtained when trimerizing cyanogen chloride.

Cyanuric chloride is an intermediate product of considerable technical importance for the production of dye stuffs, plant protection agents, pharmaceuticals as well as of textile and rubber adjuvants and is obtained after the catalytic trimerisation of cyanogen chloride in gaseous form together with unreacted cyanogen chloride and chlorine. This gas mixture is usually passed into separation chambers and the cyanuric chloride is deposited on the cooled walls thereof. It is a disadvantage of this kind of desublimation that the cyanuric chloride in the form of coarse crystals sticks to the walls and removal devices and thus has an adverse influence on heat transfer. Regular knocking off of the sticking crystals from the walls results merely in a brief improvement of the heat transfer. Moreover this method is in no way satisfactory because of the increasing mechanical damaging of the condensor and the noise, quite apart from the poor quality of the product obtained in this way.

According to Federal Republic of Germany Auslegeschrift No. 12 66 308 the attempt has been made to overcome this problem by spraying cyanuric chloride together with a readily evaporating cooling liquid, for example methylene chloride or chloroform. In this way, a finely divided cyanuric chloride is admittedly obtained but the recovery of the cooling liquid is quite laborious. Furthermore, blockages of the nozzle can occur very easily.

Instead of the direct separation of the cyanuric chloride vapor it has been proposed for example according to Federal Republic of Germany patent specifications No. 25 37 673 and 23 32 636 to liquefy the cyanuric chloride contained in the reaction gas before the solidification and then to spray, whereby the problem caused by the dissipation of the desublimation heat is smaller and whereby chlorine as well as cyanuric chloride can be removed before the separation. This two-step process is technically rather complicated. Also the processes according to the Federal Republic of Germany patent specifications No. 28 43 381 and 28 43 382 show these advantages where the reaction mixture obtained after the trimerisation of cyanogen chloride is passed into an apparatus combination comprising a removal column and a condensor, and by temperature regulation the cyanuric chloride is condensed partly in the column at the outlet of the condensor, whereas the gaseous part, which emerges at the column head, is desublimated in conventional separation chambers. This method gives rise to high investment and operational costs.

Therefore, it is an object of the present invention to provide a process for obtaining solid cyanuric chloride from the cyanuric chloride vapor obtained by trimerizing cyanogen chloride which does not possess the described disadvantages of the prior art and which renders it possible to produce a finely divided cyanuric chloride having a narrow particle distribution using simple technical means.

Thus, according to the present invention there is provided a process for obtaining solid cyanuric chloride from the cyanuric chloride vapor obtained by trimerizing cyanogen chloride wherein cyanuric chloride vapor is introduced into the center of many separated, cold, annularly disposed inert gas streams in the lower part of the condensor and wherein the solid cyanuric chloride precipitating at the bottom of the condensor is removed whereas the warm inert gas is removed at the side.

According to the process of the present invention there is, surprisingly, obtained an extremely pure cyanuric chloride with a considerably higher throughput as is possible with known processes. The so obtained cyanuric chloride is finely divided with a satisfactory distribution of the particle sizes.

According to the present invention the reaction mixture obtained in trimerizing of cyanogen chloride is introduced in the lower part of a condensor in such a manner that said reaction mixture is located in the center of many separated inert gas streams moving from the bottom towards the top. In this way it is prevented that the cyanuric chloride vapor comes in contact with the walls of the condensor and the formation of coarse crystals or agglomorates is prevented. The splitting of the inert gas stream into separated partial streams can take place with the conventional nozzles being disposed concentrically around the cyanuric chloride inlet pipe.

In a preferred embodiment of the present invention the cyanuric chloride vapor and the inert gas streams are circulated by a propulsion jet.

In an especially preferred embodiment the introduction of the inert gas streams is achieved by an annular nozzle, consisting of an annular tube having a corresponding number of holes which is called jet ring. The partial inert gas streams are introduced into the condensor through this jet ring with high speed. From this high speed of the inert gas streams there results a partial vacuum in the center of the jet ring causing a gas circulation. The gas entraining condensed cyanuric chloride particles is lifted up, turned around at the head of the condensor and is then sucked downwards at the walls and is cooled there. At the level of the tubular die the inert gas streams undergo once again a change of direction and are again turned upwards. At this moment the separation of the cyanuric chloride particles from the inert gas occurs. The greater particles are centrifuged to the bottom of the condensor by the gravitational or centrifugal force that is effective there and said particles can be removed without any problem by means of the conventional removal means. The smaller particles are sucked in once again and are transported upwards together with the circulation flow. These fine particles serve as initial nuclei accelerating the condensation of the newly entering cyanuric chloride vapor. In this way there results a very narrow particle size spectrum that can be controlled exactly by the temperature as well as by the mass stream of the inert gas.

The inert gas streams are introduced preferably at a very high speed, particularly at more than 80 m/sec. into the condensor. With particular preference, the inert gas streams are introduced into the condensor at sonic speed. The cyanuric chloride and the inert gas used as propulsion jet are circulated in the condensor due to this high speed whereby a quick mixing of the cyanuric chloride vapor with the inert gas occurs.

The inert gas streams suitably have temperature in the range of $-80°$ C. to $+100°$ C., preferably in the range of $0°$ C. to $+40°$ C. In this range of temperature the chilling effect allows in any case that the cyanuric chloride particles are condensed out in the desired finely divided form.

The mass stream ratio of cyanuric chloride vapor to inert gas is not critical and can be varied in wide ranges. Preferably, the mass stream ratio of cyanuric chloride vapor to inert gas is adjusted to 0.5 to 5, particularly 1.5 to 3.

As inert gas all gases can be used that do not react with the cyanuric chloride vapor at the respective temperatures. For economical reasons dry air or nitrogen are preferred.

The excess heated inert gas containing a small portion of finely divided particles as well as impurities of cyanogen chloride and chloride is preferably removed at the side in the lower part of the condenser. After cooling down and removal of the impurities using known methods the inert gas can be introduced into the depositor.

According to the process of the present invention there are achieved high deposit speeds and condensation throughputs respectively without sticking. Simultaneously, a very finely divided cyanuric chloride can be obtained having a powder density of less than 800 kg/m$^3$.

FIG. 1 shows a preferred embodiment of the process of the present invention. According to FIG. 1 the cooled inert gas is introduced through pipe (1) into the condenser (2) and is split into many partial high-speed streams by means of the jet ring. Into the center of these partial streams the cyanuric chloride vapor is introduced into condensor via pipe (3). After condensing the cyanuric chloride the excess heated inert gas is removed via pipe (4) and the condensed cyanuric chloride is removed at the bottom of the condenser via pipe (5).

The present invention is described by the following example without limiting the scope of the present invention:

EXAMPLE

According to FIG. 1 a test has been carried out in which cyanuric chloride was condensed under the following condition:

mass stream of cyanuric chloride: 100 parts by weight/h mass stream of inert gas: 50 parts by weight/h temperature of the introduced inert gas: 20° C. speed of the introduced inert gas: 330 m/sec.

Cyanuric chloride was obtained having a powder density of 760 kg/m$^3$.

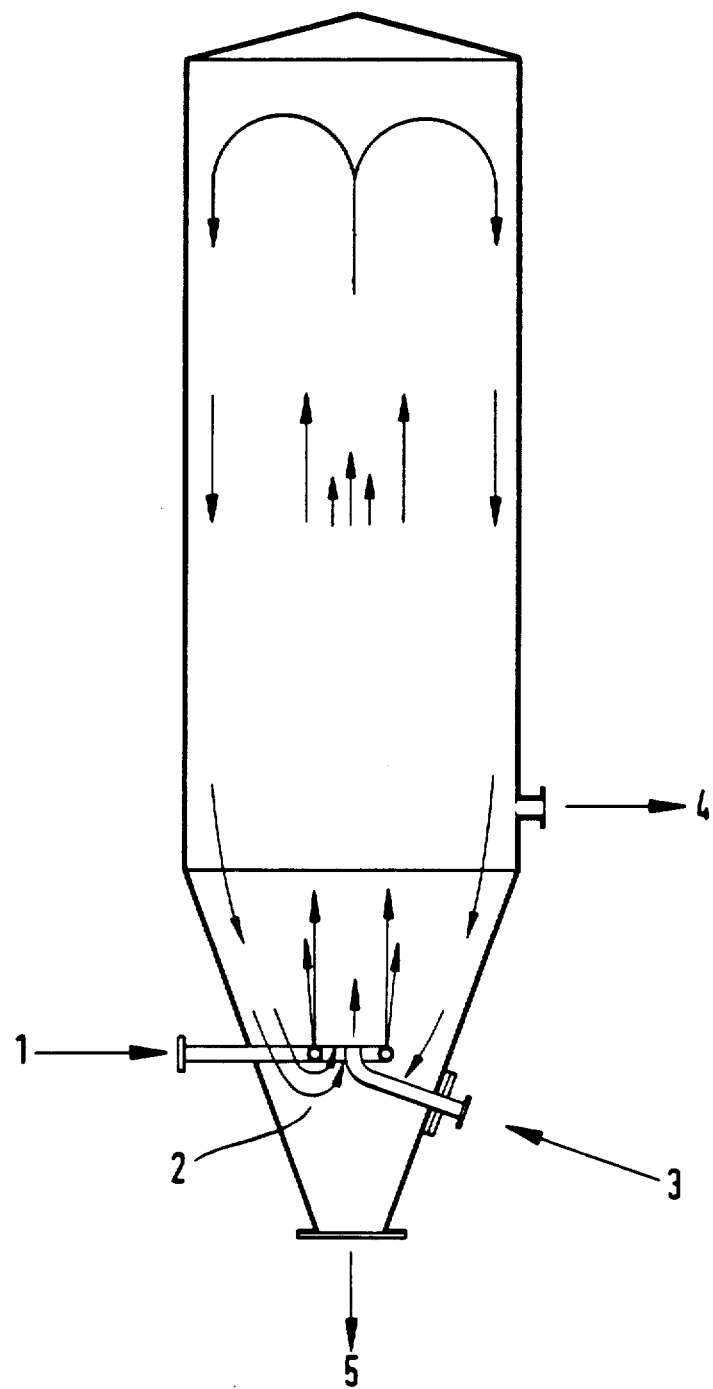

I claim:

1. In a process for obtaining solid cyanuric chloride from cyanuric chloride vapor obtained by trimerizing cyanogen chloride, the improvement, comprising: introducing the cyanuric chloride vapor into the center of a plurality of separated annularly disposed inert gas streams being substantially dry and having a temperature lower than a temperature of the cyanuric chloride vapor and disposed in the lower part of a condensor to cool and condense the cyanuric chloride vapor to a solid with the transfer of heat to the inert gas stream, and removing the condensed solid cyanuric chloride from the bottom of the condenser and the heated inert gas from the side of the condenser.

2. The process of claim 1 wherein the cyanuric chloride and the inert gas are introduced into the condenser circulated by means of a propulsion jet.

3. The process of claim 1 wherein the inert gas streams are introduced via an annular nozzle into the condensor.

4. The process of claim 1 wherein the inert gas streams are introduced at a speed of more than 80 m/sec.

5. The process of claim 1 wherein the inert gas streams are introduced at sonic speed.

6. The process of claim 1 wherein the inert gas streams are introduced at a temperature in the range of −80° to +100° C.

7. The process of claim 1 wherein the mass stream ratio of cyanuric chloride vapor to inert gas is 0.5 to 5.

8. The process of claim 1 wherein the inert gas streams are introduced at a temperature in the range of 0° C. to 40° C.

9. The process of claim 1 wherein the mass stream ratio of cyanuric chloride vapor to inert gas is 1.5 to 3.

10. The process of claim 4 wherein the inert gas streams are introduced at a temperature in the range of −80° C. to +100° C.

11. The process of claim 10 wherein the mass stream ratio of cyanuric chloride vapor to inert gas is 0.5 to 5.

* * * * *

UNITED STATES PATENT AND TRADEMARK OFFICE
CERTIFICATE OF CORRECTION

PATENT NO.  : 4,788,286
DATED       : November 29, 1988
INVENTOR(S) : Hubertus Klima It is certified that error appears in the above-identified patent and that said Letters Patent is hereby corrected as shown below:

The sole figure is inverted and should be viewed so that numerals appear right side up. (as per attached sheet)

Column 4, line 20, Claim 2 "condenser circulated" should read --condenser and circulated--.

Signed and Sealed this

Eighth Day of August, 1989

Attest:

DONALD J. QUIGG

Attesting Officer

Commissioner of Patents and Trademarks